United States Patent [19]

Pruitt et al.

[11] Patent Number: 5,170,744
[45] Date of Patent: Dec. 15, 1992

[54] LONG-TERM STORAGE OF INFECTIVE JUVENILE NEMATODES IN PSEUDOPLASTIC LAYERS

[75] Inventors: Paul L. Pruitt, Half Moon Bag; Milton J. Friedman, Belmont, both of Calif.

[73] Assignee: Biosys Corporation, Palo Alto, Calif.

[21] Appl. No.: 806,559

[22] Filed: Dec. 13, 1991

[51] Int. Cl.$^5$ .............................. A01K 29/00
[52] U.S. Cl. ...................................... 119/6.7
[58] Field of Search .................... 119/6.7, 6.6, 6.5

[56] References Cited

U.S. PATENT DOCUMENTS

| | | | |
|---|---|---|---|
| 3,391,909 | 7/1968 | Lim | 435/178 |
| 4,352,883 | 10/1982 | Lim | 435/178 |
| 4,407,957 | 10/1983 | Lim | 435/178 |
| 4,409,331 | 10/1983 | Lim | 435/178 |
| 4,417,545 | 11/1983 | Finney | 119/6.6 |
| 4,615,883 | 10/1986 | Nelsen et al. | 119/6.7 X |
| 4,647,536 | 3/1987 | Mosbach et al. | 435/177 |
| 4,663,286 | 5/1987 | Tsang et al. | 435/178 |
| 4,701,326 | 10/1987 | Nelsen et al. | 119/6.7 X |
| 4,753,799 | 6/1988 | Nelsen et al. | 119/6.7 X |
| 4,765,275 | 8/1988 | Yukawa et al. | 119/15 |
| 4,778,749 | 10/1988 | Vasington et al. | 435/2 |
| 4,798,786 | 1/1989 | Tice et al. | 435/177 |
| 4,803,168 | 2/1989 | Jarvis, Jr. | 435/240 |
| 4,806,355 | 2/1989 | Goosen et al. | 424/424 |
| 4,814,274 | 3/1989 | Shioya et al. | 435/174 |

FOREIGN PATENT DOCUMENTS 256873  2/1988  European Pat. Off.

*Primary Examiner*—Gene Mancene
*Assistant Examiner*—Thomas Price
*Attorney, Agent, or Firm*—Morrison & Foerster

[57] ABSTRACT

Infective juvenile nematodes can be stored for long periods of time when contained in a layer having pseudoplastic characteristics. The pseudoplastic layer immobilizes the infective juveniles, but the pseudoplastic nature of the compositions permits easy dispensing of the composition when required. Suitable pseudoplastic agents include rhamsan gum and xanthan gum.

21 Claims, 2 Drawing Sheets

LONG-TERM STORAGE OF INFECTIVE JUVENILE NEMATODES IN PSEUDOPLASTIC LAYERS

TECHNICAL FIELD

The invention relates to techniques for storing entomogenous nematodes in the infective juvenile stage for later use as agricultural pest control agents. More specifically, the invention concerns formulating and packaging infective juveniles into pseudoplastic layers for prolonged storage and convenient dispensation when use is desired.

BACKGROUND ART

The desirability of using entomogenous nematodes in compositions to control pests in agricultural contexts has been clearly recognized. The general classification "nematodes" includes roundworms of astounding variety ranging in size from ultramicroscopic to worms of several feet in length. In many cases, these organisms are parasitic, and their mechanisms of parasitism and their targets are as varied as their size range. Plant pathogenic nematodes are a recognized agricultural nuisance, and various toxic compounds have been formulated to control their growth. Parasitic diseases in animals and humans caused by these parasites include heartworm in dogs and river blindness in humans.

However, a relatively benevolent group of nematodes infects insects that are themselves agricultural pests, and thus this group is seen as having a useful function. In particular, control of insect infestation of plants has been attempted using the "infective juvenile" stage of these entomogenous nematodes. In this form, the infective juvenile or "IJ" enters the host insect through the alimentary canal or spiracles, emerges from its protective sheath, and penetrates into the host insect's hemocoel. In the host insect's hemocoel the nematode releases symbiotic bacteria which induce septicemia that kills the host and renders the host corpse suitable for nematode foraging and reproduction. Several generations may be spent within the insect host until food consumption and overpopulation trigger production of another IJ stage generation. The new infective juveniles must then find fresh hosts.

In the infective juvenile stage, the nematodes do not eat, but depend upon internal food stores; however, they do require oxygen, and, unless induced into a cryptobiotic desiccated state, require the presence of water.

A major problem associated with the use of infective juvenile nematodes as pesticides resides in the necessity to maintain the infective juveniles in a viable state for extended time periods. The infective juveniles cannot be kept viable simply by harvesting them from, for example, an artificial culture, and placing them in a container. The majority of the infective juveniles so prepared will die within a few hours. Various attempts have been reported to overcome this problem; these attempts fall generally into two categories. In one approach a "cryptobiotic" state is induced by dehydration or other means so as to reduce the metabolism to the point where the infective juvenile essentially becomes inert. It is known that nematodes in the soil may exist in such a cryptobiotic state under dry climatic conditions; however, the statistics of this process are not favorable to preserving large numbers of infective juveniles. Alternative drying means which result in a cryptobiotic state with some degree of efficiency are described, for example, in European Patent Application published as Publication No. 256,873.

In an alternative approach, the IJs are stored on various moist, high surface area materials. For example, U.S. Pat. No. 4,417,545 describes a method and package for storage and shipment of nematodes which comprises essentially a foam sandwich wherein the foam retains water. While the container is stated to be "suitable for storing nematodes", only nematode eggs were tested, and only one particular foam was found to be successful in maintaining the viability of the eggs, even when storage was at the low temperature of $-5°$ C.

U.S. Pat. No. 4,765,275 also describes a packaging system for nematode storage and transport. In this proposal, the nematodes are stored as a suspension in a manner so as to prevent microbial growth (such as by adding formaldehyde to the suspension) and in the presence of an adsorbent, such as activated charcoal.

U.S. Pat. No. 4,615,883 describes a formulation of infectious juveniles in which the IJs are encapsulated in an alginate gel obtained by adding calcium ion to a sodium alginate suspension of the nematodes. In these preparations, capsules of 0.5-5 mm in diameter are formed and are said to improve the storageability of the IJs. The use of alginate gels and other encapsulating materials to encapsulate living tissue or cells (though not specifically IJs) has an extensive literature. See, for example, U.S. Pat. Nos. 4,409,331; 4,407,957; 4,391,909; 4,352,883; 4,663,286; 4,778,749; 4,798,786; 4,803,168; 4,806,355; 4,647,536; and 4,814,274. All of these patents describe methods to encapsulate living cells or tissues in various polymeric capsules. The purpose of the capsules in each case is to preserve the viability of the living tissue and, also, to facilitate the use of such tissue in its intended application.

U.S. application Ser. No. 07/313,594, filed Feb. 21, 1989, assigned to the same assignee and incorporated herein by reference, describes a packaging method for IJs in a reversibly cross-linked matrix which is embedded in a supporting screen. The screen containing the sheet matrix is simply placed in the location of end use, and application of water and an active decross-linking agent liberates the embedded nematodes from the film.

It has now been found that a more convenient and effective manner of preserving the viability of infective juveniles resides in immobilizing the IJs in a pseudoplastic gel, which can then readily be dispensed in the field by applying a suitable shear force. While embedded in the matrix, the IJs are immobilized, resulting in reduced metabolism and improved viability. However, upon liquefaction of the supporting medium, the IJs can be readily dispensed in the desired location.

DISCLOSURE OF THE INVENTION

The invention provides a convenient formulation and packaging means for storing, shipping, and dispensing infective juvenile nematodes which are capable of entomogenous activity. The invention methods offer convenience and effectiveness and are suitable for large-scale production and distribution of IJs.

Thus, in one aspect, the invention is directed to a method of storing entomogenous nematodes, which method comprises mixing a suspension of infective juvenile entomogenous nematodes with a pseudoplastic agent to form a pseudoplastic mixture. The mixture is then formed into a layer which is suitably positioned within a gas-permeable envelope. The envelopes are then stored in a manner that maintains the integrity and dimensions of the pseudoplastic layer.

In another aspect, the invention is directed to a nematode formulation for prolonged storage which comprises a layer of a pseudoplastic mixture wherein the mixture comprises a pseudoplastic agent and a suspension of the nematode IJs. The layer may be packaged in envelopes for convenient storage. Thus, in another aspect, the invention is directed to a package containing the pseudoplastic mixture of suspended IJs.

In still another aspect, the invention is directed to a method to apply nematodes to a desired location, which method comprises applying shear force to the formulated layers of the invention and thereby dispensing the liquefied formulation.

MODES OF CARRYING OUT THE INVENTION

As set forth in the Background section hereinabove, only certain members of the "nematode" classification are capable of parasitizing and killing insects. The most commonly used species for this purpose is *Steinernema carpocapsae*, also known as *Neoplectana carpocapsae*. Also particularly useful are *S. feltiae* (*N. bibionis*), *N. glaseri*, *S. scapterisci*, *Heterorhabditis heliothidis* and *H. bacteriophae*. Additional species include: *N. menozzi* (*Steinernema kraussei*), *N. kirjanovae* (*Steinernema glaseri*), *N. georgica* (*Steinernema bibionis*), *N. dutkyi*, *Heterorhabditis bacteriophora*, *H. boptha*, *H. hambletoni*, *Filipjevimermis leipsandra*, *Reesimermis nielseni* (*Romanomermis culicivorax*), *Diximermis petersoni*, *Hexamermis arvalis*, *Mermis nigrescens*, and *Pheromermis pachysoma*.

The foregoing list is not exhaustive, and the method of the invention is applicable to the infective juvenile stage of entomogenous nematodes in general. "Infective juvenile" or "IJ" refers to an entomogenous nematode usually in the third larval stage characterized by retention of the second stage cuticle or sheath after molting to the third stage. In this stage of their development, IJs are capable of vertical and horizontal migration, but depend on internal food stores and do not eat.

Methods for culturing entomogenous nematodes to obtain larvae in the IJ state are known. In general, it was long thought necessary to provide a substrate-supported medium containing the symbiotic bacteria which are necessary for the IJs to exhibit their entomogenous effect. However, more recently it has been found possible to culture such IJs in liquid medium. See, for example, U.S. Pat. No. 5,023,183. The nematodes are grown by any convenient method to the infective juvenile stage, harvested using standard procedures and suspended in water or buffer usually at a concentration of about $1 \times 10^5$–$2 \times 10^6$ IJs/ml for preparation of the formulations of the invention.

Figure 1:
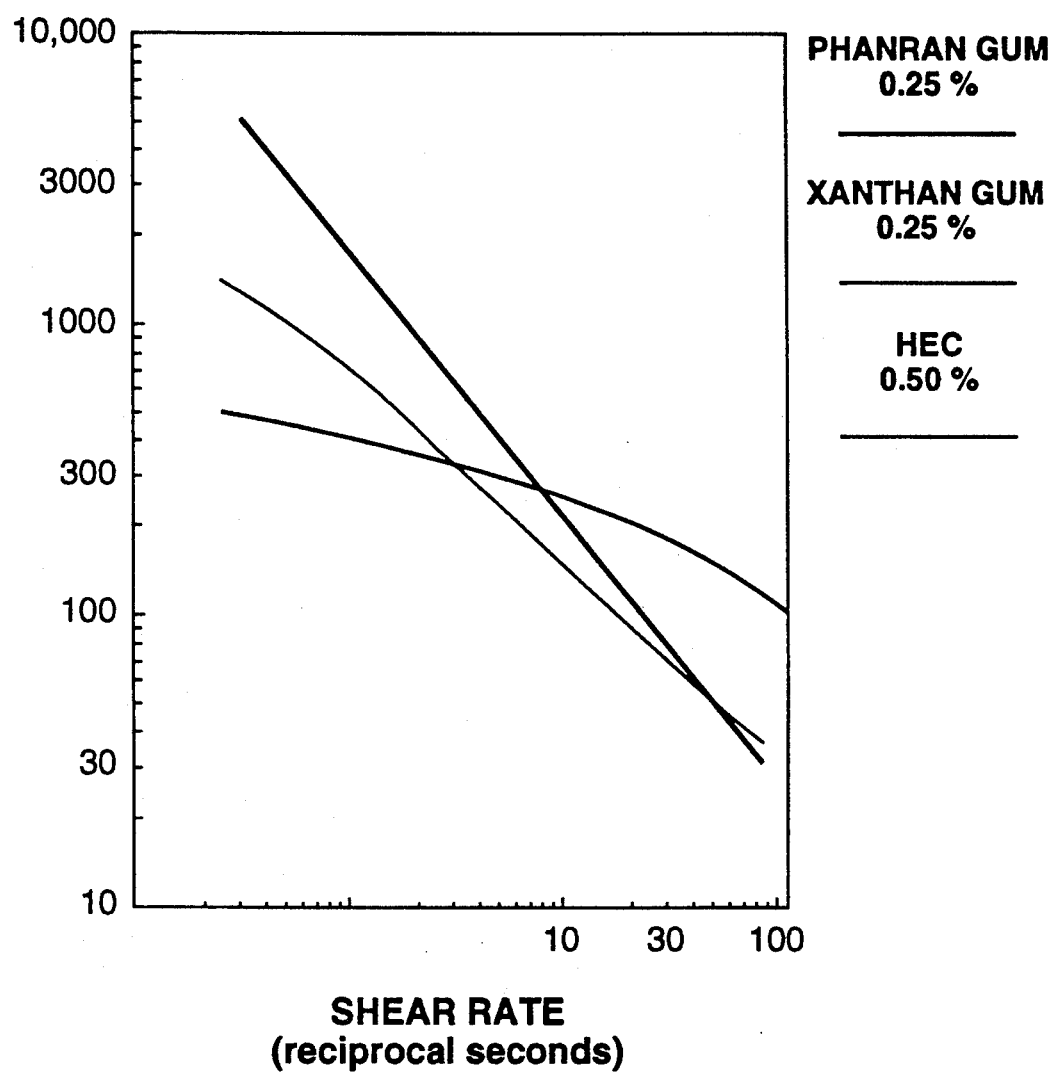
FIG. 1 shows an illustrative graphical representation of the viscosity properties of pseudoplastic and nonpseudoplastic media.

The suspension of harvested nematodes is then mixed with a pseudoplastic agent. A pseudoplastic agent is a material which, when used to form a pseudoplastic mixture, results in a mixture wherein the viscosity is roughly inversely proportional to shear rate. A general discussion of pseudoplasticity is provided in "More Solutions to Sticky Problems" (1989) published by Brookfield Engineering Laboratories, Inc., Stoughton, Mass. Suitable pseudoplastic agents include, for example, rhamsan gum, marketed by Kelco (Merck & Co., Rahway, N.J.), and xanthan gum. FIG. 1 shows a typical representation of the pseudoplastic properties of a 0.25% solution of rhamsan gum or 0.25% xanthan gum in comparison with the poorly nonpseudoplastic agent hydroxyethylcellulose (HEC) at 0.5% concentration. As seen in FIG. 1, the viscosity of the rhamsan gum solution increases linearly with decrease in shear rate when plotted on a log-log scale. Xanthan gum is less effective, but still pseudoplastic; the HEC curve shows a viscosity which is almost independent of shear rate.

As used herein, "pseudoplastic" mixture refers to a mixture wherein the viscosity of the mixture increases by a factor of at least 10 over a 100-fold decrease in shear rate, as illustrated in FIG. 1.

In preparing the formulations of the invention, the suspension of nematodes is mixed with the pseudoplastic agent, or a solution thereof, wherein the pseudoplastic agent is supplied at a concentration sufficient to obtain a pseudoplastic mixture as defined above. The pseudoplastic mixture will generally contain the pseudoplastic agent at a final concentration of about 0.05–1% wt/vol, and is preferably formulated with a bactericide or fungicide to prevent infection, wherein said antibiotic is not toxic to the nematodes. One suitable antibiotic is "Proxel" (1,2-benzisothiazoin-3-one). The mixture is then layered using any desired casting or forming means. Preferably the layer is formed by pumping the mixture into a gas-permeable, water-impermeable pouch, sealing the pouch, and positioning the pouch to allow the mixture to form a thin layer of about 0.5–5 mm. Alternatively, the layering can be effected by applying the mixture to a water-impermeable support and spreading the applied mixture mechanically with a spreader into a thin film. Removing the shear pressure of the spreading action results in a viscosity increase in the film so as to obtain a layer capable of immobilizing the suspended nematodes, but wherein the layer is sufficiently thin to secure an adequate oxygen supply. Suitable thicknesses for such layers are about 0.5 mm–5 mm. Convenient dimensions for the layer are on the order of about 20–40 square inches.

The layers can be packaged conveniently in sealed envelopes made of materials which are sufficiently permeable to oxygen to permit respiration by the suspended nematodes. The material composing the envelope should be sufficiently impermeable to water that not more than 1 g of water/$m^2$/day is lost. Suitable materials for the envelope include polyolefins, such as low or high-density polyethylene, or fluorinated ethylene propylene copolymers. If formed of such flexible materials, the envelopes can conveniently be sealed by heat sealing. The mixture is then dispensed by severing the envelope. Application of shear force, then, to the contents of the envelope permits ready dispensation of the formulation.

Figure 2A:
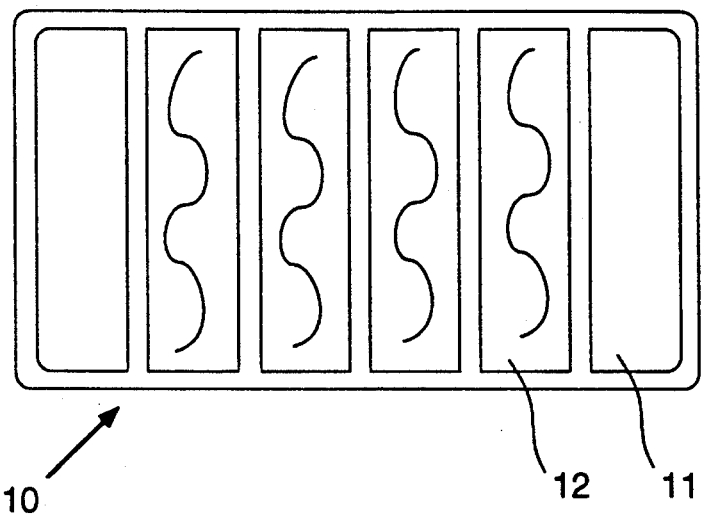
FIGS. 2A–2C show an illustrative packaged-layer formulation of the invention.
Figure 2B:
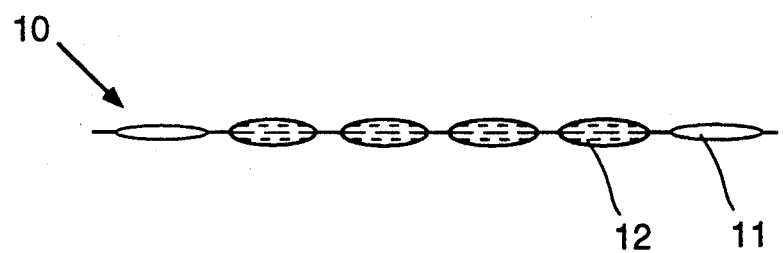
Figure 2C:
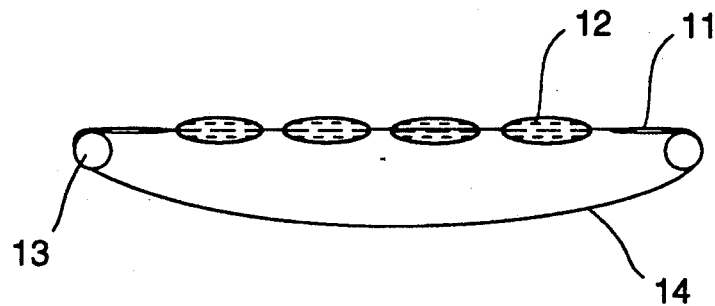

A typical configuration of the package is shown in FIG. 2. FIG. 2A shows a front view of a low-density polyethylene envelope (Attane 4003, manufactured by Dow Chemical Co.) 10 which provides a multiplicity of compartments 12 filled with the pseudoplastic mixture containing nematodes of the invention. The compartments containing the mixture are sealed. Filling of the compartments is straightforward as the shear force of transferring the pseudoplastic mixture to the package is sufficient to achieve the necessary flow rate. A section at each end of the envelope 11 is not filled with mixture. The flexible pouch or envelope, shown end-on in FIG. 2B, is then flattened to maintain a stable layer. A convenient manner of achieving this stable layer is shown in FIG. 2C. The multicompartment envelope 10 is placed across a spring-form support 12 made of a plastic such as polycarbonate to which polycarbonate rods 13 have been glued. The envelope 10 containing the nematode formulation is then glued over the ends of the polycarbonate rods 13 with the support 12 in the flexed position. The support 12 is then released and allowed to extend, applying lateral extension force to the envelope 10. The support 12 can be retained in storage.

Of course, other ways of achieving the immobilized thin layer of nematodes contained in the pseudoplastic mixture will be apparent to those of skill in the art. For example, a storage rack containing a multiplicity of layers across which the envelopes are placed, wherein one side of the rack is adjustable offers a convenient alternative.

The envelopes are then preferably stored horizontally to prevent settling of the nematodes in the layer and to prevent settling of the pseudoplastic mixture itself. Settling can also be prevented by addition of a stabilizing agent to the formulation. Such stabilizing agents will be inert with respect to the biological activity of the infective juveniles and will not affect the pseudoplasticity of the mixture. Suitable stabilizing agents are preferably high concentrations of carbohydrate materials, such as 10-20% sucrose or 20-30% dextran. Addition of stabilizing agent mitigates necessity for horizontal storage and enhances the convenience of the formulation. The density should be 1.03–1.1 g/ml.

The nematodes formulated as set forth herein may be stored at temperatures as high as 28° C. for more than one week, but lower temperatures permit longer periods of maintenance.

The following examples are intended to illustrate but not to limit the invention.

PREPARATION A

Growth and Harvest of IJs

The nematodes were grown to the infective juvenile stage as described in U.S. Pat. No. 5,023,183, incorporated herein by reference. The organisms were harvested by centrifugation and suspended in water at a concentration of $150 \times 10^6$ in 200 mls.

EXAMPLE 1

Formulation of IJs into a Pseudoplastic Mixture

Rhamsan gum (Kelco K7C233) (0.5 gm) was blended with 100 ml of water containing 0.5% Proxel GXL in a Waring-type blender for 10 min. 50 gm of the blended material was added to the slurry of 150 million *Steinernema carpocapsae* IJs in 200 ml of water of Preparation A and mixed with a wire whisk Kitchenaid mixer for 30 min. The viscosity of the resulting mixture was 1160 cp at a shear rate of 0.4 sec and 70.5 cp at a shear rate of 40 sec.

EXAMPLE 2

Packaging of the Pseudoplastic Mixture Containing IJs

Four 3.8 cm×3.8 cm pouches made from 1 mil thick film of Attane 4003 (Dow Chemical Co.) were fabricated using standard impulse-heat sealing equipment and each filled with 2.23 ml of the slurry produced by the method of Example 1.

The pouches were stored at 25° C. on a flat surface of polypropylene foam. After 4 months of storage, 93% of the nematodes were still alive.

EXAMPLE 3

Multipouch Packages

A finished multipouch package, as shown in FIG. 2, containing formulated nematodes was fabricated containing four 3 cm×8 cm compartments separated by 1.5 mm seals and flanked by 3 cm of excess film material on each side. A plastic holder was constructed from a 15 cm×11 cm×1.6 mm sheet of polycarbonate with 6 mm polycarbonate rods glued along the 11 cm edges. The pouch was assembled on the holder by bowing the sheet by approximately 1 cm in the longest dimension and gluing the pouch across the bow with polymer adhesive.

EXAMPLE 4

Alternative Formulations and Packaging

The procedure of Example 1 was used to prepare formulations which contain 600,000 *S. carpocapsae* IJs in 0.1% rhamsan gum with 0.1% proxel. Formulation A contains no stabilizing agent, formulation B contains 25% dextran, and formulation C contains 15% sucrose.

Each formulation (7 ml) was poured into a 3×8 cm pouch, stored vertically, but stretched flat to a depth of about 3 mm. After 2 days, formulation A without stabilizer showed visible settling; however, formulations B and C did not.

EXAMPLE 5

Using the procedure set forth in Example 1, a formulation containing $250 \times 10^6$ *S. carpocapsae* IJs, 0.1% proxel, and 0.2% xanthan gum (Keltro T , Kelco, USA) mixed with water to 46 grams was prepared.

What is claimed is:

1. An entomogenous nematode formulation for prolonged storage of infective juveniles of said entomogenous nematodes, which formulation comprises a pseudoplastic mixture layer, said pseudoplastic mixture layer comprising a pseudoplastic agent and a suspension of a multiplicity of said infective juvenile entomogenous nematodes.

2. The formulation of claim 1 wherein said pseudoplastic agent is rhamsan gum or xanthan gum.

3. The formulation of claim 1 wherein said layer contains about $10^5 - 2 \times 10^6$ infective juveniles per ml.

4. The formulation of claim 1 which further contains a stabilizing agent to provide a specific gravity of 1.03–1.1 g/ml.

5. The formulation of claim 4 wherein said stabilizing agent is 10–20% sucrose or 20–30% dextran.

6. The formulation of claim 1 wherein said layer is contained in a sealed water-impermeable, oxygen-permeable flat compartment.

7. The formulation of claim 6 wherein said sealed flat compartment is contained in an approximately two-dimensional envelope array comprised of a multiplicity of said sealed compartments.

8. The formulation of claim 1 wherein said infective juveniles are of the family *Steinernematidae* or *Heterorhabditidae*.

9. A method to prepare a storage formulation of infective juvenile entomogenous nemotodes, which method comprises mixing a suspension of said infective juveniles with a solution of a pseudoplastic agent to form a pseudoplastic mixture containing said nematodes and forming said mixture into a layer.

10. The method of claim 9 wherein said forming into a layer is effected by spreading said mixture onto a surface coated with a water-impermeable film.

11. The method of to claim 9 wherein said forming into a layer is effected by placing said mixture in water-impermeable, oxygen permeable flat compartment and positioning said compartment in a horizontal position.

12. The method of claim 9 wherein said pseudoplastic agent is rhamsan gum or xanthan gum.

13. The method of claim 9 which further comprises including said layer in a sealed water-impermeable, oxygen-permeable flat compartment.

14. The method of claim 13 wherein said sealed flat compartment is contained in a substantially two-dimensional envelope array comprised of a multiplicity of said sealed compartments.

15. The method of claim 9 wherein said suspension contains about $10^5 - 2 \times 10^6$ infective juveniles/ml.

16. The method of claim 9 wherein said infective juveniles are of the family *Steinernematidae* or *Heterorhabditidae*.

17. A package for storing infective juvenile entomogenous nematodes, which package comprises a sealed water-impermeable oxygen-permeable flat compartment containing a layer comprising a pseudoplastic mixture of said infective juveniles, said pseudoplastic mixture comprising a pseudoplastic agent.

18. The package of claim 17 wherein said pseudoplastic agent is rhamsan gum or xanthan gum.

19. The package of claim 17 wherein said sealed compartment is contained in a substantially two-dimensional envelope array comprised of a multiplicity of said sealed compartments.

20. The package of claim 17 wherein said layer contains about $10^5 - 2 \times 10^6$ infective juveniles/ml.

21. The method of claim 20 wherein said infective juveniles are of the family *Steinernematidae* or *Heterorhabditidae*.

* * * * *